United States Patent
Bellipanni

(10) Patent No.: US 8,501,203 B2
(45) Date of Patent: Aug. 6, 2013

(54) TOPICAL FORMULATION FOR THE TREATMENT OF CELLULITE

(75) Inventor: Giulio Bellipanni, Rome (IT)

(73) Assignee: Chronolife S.r.l., Rome (IT)

( * ) Notice: Subject to any disclaimer, the term of this patent is extended or adjusted under 35 U.S.C. 154(b) by 308 days.

(21) Appl. No.: 12/733,453

(22) PCT Filed: Sep. 2, 2008

(86) PCT No.: PCT/IT2008/000567
§ 371 (c)(1),
(2), (4) Date: May 13, 2010

(87) PCT Pub. No.: WO2009/040851
PCT Pub. Date: Apr. 2, 2009

(65) Prior Publication Data
US 2011/0280962 A1 Nov. 17, 2011

(30) Foreign Application Priority Data
Sep. 4, 2007 (IT) .............................. RM2007A0456

(51) Int. Cl.
*A61K 8/02* (2006.01)
*A61K 8/97* (2006.01)

(52) U.S. Cl.
USPC ..................... 424/401; 424/78.03; 424/78.05; 514/860; 514/887

(58) Field of Classification Search
USPC ................... 424/401, 78.03, 78.05; 514/860, 514/887
See application file for complete search history.

(56) References Cited

U.S. PATENT DOCUMENTS

| | | | | |
|---|---|---|---|---|
| 5,770,223 | A | * | 6/1998 | Bonte et al. .................... 424/450 |
| 2004/0142007 | A1 | | 7/2004 | Moussou |
| 2006/0275218 | A1 | * | 12/2006 | Tamarkin et al. ............... 424/45 |

FOREIGN PATENT DOCUMENTS

| | | | |
|---|---|---|---|
| EP | 0803246 | * | 10/1997 |
| FR | 2571256 | * | 7/1984 |
| FR | 2578165 | A | 9/1986 |

OTHER PUBLICATIONS

International Search Report Dated Sep. 2, 2009.
Lackey D.: "Isolation and structural determination of a novel TRH like tripeptide, pyro-Glu-Tyr-Pro-0 amide, from alfalfa", retrieved from the Internet Jan. 26, 2009 URL:http//cat.inist.fr/?aModele=afficheN&cpsidt=4811329>.

* cited by examiner

*Primary Examiner* — Mina Haghighatian
(74) *Attorney, Agent, or Firm* — Hedman & Costigan, P.C.; James V. Costigan

(57) ABSTRACT

The present invention concerns a topical formulation for the treatment of cellulite, comprising alfalfa herb and derivatives thereof and can further comprise melatonine.
The invention refers also to a method of application of said formulation and to a pharmaceutical kit for the treatment of cellulite comprising said formulation, together with vegetal or mineral mud.

1 Claim, No Drawings

TOPICAL FORMULATION FOR THE TREATMENT OF CELLULITE

The present invention concerns a topical formulation for the treatment of cellulite.

More in particular, the invention refers to a creamy pharmaceutical formulation, suitable to be administered cutaneously, preferably in association with thermal muds.

It is known that cellulite is a disease that involves the hypoderm, tissue of a predominantly adipose nature placed between the dermis and the underlying muscular layer, of some specific anatomic regions in women and men.

Cellulite typically imparts an "orange peel" appearance to the skin and is due to the increase in the subcutaneous layer of the number and dimension of the cells of fat positioned below the derm.

It is commonly agreed that one of the most important causes of the appearance of cellulite is the reduced vascularization of the muscular layer that is just below the adipose component. The reduction of the vascularization causes the reduction of the lipoilstic hormonal signals to the superficial fat. Moreover, for this reason the superficial fat responds weakly to therapeutic intervention.

Cellulite is a disease having an evolutive character, which develops from anatomic, hormonal and metabolic features, in conjunction with events such as a wrong diet, sedentariness, venous pathologies and hormonal therapies.

A certain relation exists between the appearance or the aggravation of cellulite and some hormonal imbalance, which are considered to be actual pathologies, but as are considered to be due to the reduced function of some glands, such as thyroid or pancreas, caused for example by an increased production of insulin, stimulated by an excess of sugars, the taking of progestens as therapeutic agents or contraceptives, the therapeutic taking of cortisones or by an abnormal surrenalic response to different stressing stimula.

It is also understood that there is a definite link between food, wellbeing and cellulite, that is influenced by the balance between correct nutrition and hormonal function.

The requirements for the appearance of cellulite in the interested regions are caused by the coexistence of problems of the venous and lymphatic microcirculation.

At present, different kinds of treatment exist for this disease, including treatments of exclusive competence of a physician, such as for example all those methods providing for the subcutaneous infiltration of substances having a draining and/or reducing effect, aesthetic treatments, such as for example massages, lymphodraining, electrostimulation, and also product for a "do it yourself" application, such as for example creams or gels performing a draining, lipolytic and vasoprotective action.

In particular products of the kind "do-it-yourself" are particularly widespread, both for the ease of application and for reduced costs.

Nevertheless, the results that can be obtained through this kind of a product are very limited, since they can not act directly on the causes of the insurgency of cellulite, but simply try to conceal its effects.

It would be much better to provide a pharmaceutical formulation, for topical use, that can be easily applied to the body in a "do-it-yourself" way, but allowing to achieve really appreciable results.

These and other results are obtained according to the present invention by providing for a creamy pharmaceutical formulation, suitable to be administered cutaneously, the action of which is based on the combination of two active principles never used before for this kind of treatment.

An aim of the present invention is therefore that of providing a pharmaceutical formulation allowing to overcome the limits of the anti-cellulite products according to the prior art and to obtain the results described previously.

A further aim of the invention is that said formulation can be realized with substantially limited costs, as far as both the costs of the used compounds and the costs of production is concerned.

It is therefore a first specific object of the present invention a topical formulation for the treatment of cellulite comprising alfalfa herb and derivatives thereof and preferably melatonin.

In particular, according to the invention, said alfalfa herb derivatives comprise the pyroGlu-Tyr-Proamide tripeptide.

According to the present invention, said alfalfa herb is present according to a concentration comprised between 5 and 40% (preferably between 10 and 20%) by weight and the concentration of said melatonin is comprised in a range between 0 and 0.1% by weight, and preferably is comprised in a range between 0.01 and 0.05% by weight.

Moreover, according to the invention, said formulation further comprises water, excipients and other natural substances, chosen amongst ginkgo bilobate, avocado, blueberry, centella, fucus, glycerine, caffeine, extract of *Centella asiatica*, escine, tocopherol, dextrin, lecithin, tocopherol acetate, phospholipids, cyclodextrins, oils and natural active principles.

Further it is a second specific object of the present invention a method for the application of a topical formulation for the treatment of cellulite as previously defined, wherein said formulation is applied on the skin, in the zones having cellulite and/or localised adiposity, by massaging until the complete absorption of the formulation.

Preferably, according to the invention, after the application of said formulation, on the zones of skin previously treated vegetal or mineral mud is applied, in case enriched with melatonin and/or alfalfa herb, and further with excipients chosen between ginkgo bilobate, avocado, blueberry, centella, fucus, zinc oxide, glycerine, caffeine, tocopherol, lecithin, waterpuncite, silica aluminate, sepiolite, essences and natural active principles, seaweeds, active thermal water.

Moreover it is a further specific object of the present invention a pharmaceutical kit for the treatment of cellulite comprising a formulation as previously defined, together with vegetal or mineral mud, preferably charged with alfalfa herb and even more preferably also with melatonin.

Further, said vegetal or mineral mud can further comprise excipients chosen between ginkgo bilobate, avocado, blueberry, centella, fucus, zinc oxide, glycerine, caffeine, tocopherol, lecithin, waterpuncite, silica aluminate, sepiolite, essences and natural active principles, seaweeds, active thermal water.

Finally, according to the invention in the mud of said pharmaceutical kit said alfalfa herb is preferably present according to a concentration comprised between 5 and 10% by weight and said melatonin is present according to a concentration comprised between 0.001 and 0.005% by weight.

The invention will be described in the following for illustrative, non-limitative purposes, with particular reference to some illustrative examples.

The pharmaceutical formulation for the treatment of cellulite according to the present invention is provided as a cream for topical application.

The cutaneous and transdermic administration of substances or medicaments is a very common way for the administration of pharmaceuticals and medicaments, is a very practical method and in some cases it represents the primary choice due to the immediate effectiveness and the good general tolerability. The active principle is applied on the affected skin according to preset procedures, such as for example rubbing or massages, in order to provide a homogeneous distribution and penetration in the pores of the skin down to the deeper layers of the subcutis and of the derma.

EXAMPLE 1

Characterization of the Active Principles of the Formulation

Active principles contained in the cream are alfalfa herb and melatonin of vegetal origin.

Alfalfa herb, or medicago sativa or medical herb, belongs to the family of leguminosae, and is generally used as nourishment for herbivores. It is rich in minerals, it is valuable for its high content of vitamin A, a vitamin that is liposoluble in fats, and consequently remains substantially unimpaired also when it is dried. Alfalfa has in 100 grams 8000 U.I. of vitamin A. It is a good source of pyridoxine, one of the vitamins of the B complex, and of vitamin E, it is rich in vitamin K and proteins, containing a percentage by weight of 18.9%.

Alfalfa herb also contains soluble and insoluble fibres, saponins, medicagenic acid, phytoestrogens, coumestrol, pigments, antioxidant activity, beta.-carotene, chlorophyl, mineral salts, other vitamins, in particular vitamins C, D, K, B1, B2, B3, B5, B6, B8, B12, folic acid. It is also rich in aminoacids.

It further contains high amounts of some coumarinic and mineral derivatives such as phosphorus, silica, sodium, potassium, calcium, magnesium, boron, iron, manganese, copper, cobalt and sulfur.

Moreover, alfalfa herb contains also triterpenic saponins, eteroxides, proteins; its aerial parts contain coumestrol, a structure similar to estradiol, with estrogenic features.

In addition to the vitamins and minerals, alfalfa herb contains also enzymes, coumestrol, isoflavones and phytoestrogens, and alkaloids such as asparagine and trigonelline.

Amongst the known effects of alfalfa herb is a-well acknowledged ipolipenic effect. In particular alfalfa herb prevents the formation of atheroma in presence of hypercholesterolemia.

The second fundamental active principle of the formulation according to the present invention is melatonin.

Melatonin is produced by the pineal gland under control of the light and is mainly excreted by night. Its excretion profile defines the biological night Light also determines different non visual responses, such as the phase shift of the internal biological clock by increasing care, heart frequency and pupilla constriction. Both estrogen, melatonin and light, if suitably administered, can therefore modify the human circadian rhythm. These effects of melatonin and light are defined chronobiotic effects and are used to relieve troubles of the circadian rhythms, such as for example those due to jetlag, night working shifts, and some sleep disorders.

Most of the physiological parameters (body temperature, hormones and electrolytes) and behavioural parameters (mood, alimentation, surveillance, sleep and performance) show circadian rhythms.

Circadian rhythms are endogenous rhythms with a periodicity of about 24 hours remaining constant in constant ambient condition (light, temperature and posture). The endogenous circadian timing system allows to the body to anticipate daily modifications of the environment. Circadian rhythms are generated by a pacemaker positioned in the superchiasmatic hypothalmic nucleus (SNC) and the damaging of these nuclei produces arrhythmias in different controlled systems.

Synchronization of such rhythms allows the regular development of common daily activities (sleep and alimentation).

Ocular light is the highest stimulus responsible of the synchronization of the circadian system in man. Even if also other stimula can act as a pacemaker for the internal clock (eating physical activity and sleep), light is the strongest primary system of regulation.

The production of endogenous melatonin is intimately linked to the circadian timing system. The rhythm of synthesis of melatonin is controlled by the superchiasmatic nucleus (SNC) by means of a multisynaptic way (SNC—paraventricular nucleum PVN—upper cervical ganglium—release of noradrenaline from postgangliar fibres in the pineal gland).

The production of melatonin is highest during darkness in all studied animal species.

Melatonin is metabolized mainly in the liver through the cytochrome P450 which transforms melatonin into 6-hydroxymelatonin. It is then conjugated with sulphate to form 6-sulphatoxymelatonin and in minor part with glycuronic acid.

Time period of the rhythm of the melatonin is considered the most reliable detector of the biological clock. Melatonin, in plasma or also in saliva, provides for a suitable and reliable instrument for long time monitoring of the human circadian system, both in laboratory and in real life.

The synthesis of melatonin is influenced by a plurality of factors, for example by physical activity, sleep, time of meals and kind of meals, stress, menstrual cycle. On the contrary, other circadian rhythms, such as body internal temperature and cortisol excretion, were significantly modified by these factors.

Melatonin is a strong antioxidant with a very good action of stimulus of the immune system. It has an important role together with other substances in maintaining the equilibrium of the neuro-immuno-endocrine system.

EXAMPLE 2

Characterization of the Mud Applicable after the Formulation According to the Invention In a preferred embodiment of the present invention, the action of melatonin and alfalfa herb based product administered cutaneously for the treatment of the cellulite is followed by the application of thermal muds on the same region of skin (in particular those coming from Abano-Montegrotto Terme) that were tested and proved to be particularly suitable because of their ability to act as a natural bio-reactor that can favor the trans-dermic passage of the cutaneously administered medicaments, with the aim of increasing the therapeutic effect.

Thermal medicine has an ancient tradition in treatment of a number of muscular-sinew, articular, skeletal and metabolic pathologies, it is predominantly used in neurology, orthopaedics and traumatology, rheumatology, endocrinology, otorhinology etc. Each of these sectors of medicine has specific indications of use with documented clinical results.

Generally, by bioreactor it is intended a container having specific functions, which is able to subject biological material possibly contained in it to influences of a chemical, physical, thermal and mechanical nature that change the state or composition or structure of the biological material.

Some thermal muds, because of the special features they have, can be compared to a natural bioreactor, that is able to subject the individual to chemical, physical, thermal and mechanical stimulations taking place at the same time, so to cause anatomical physiological, metabolic and functional modifications at the level of skin and derma superficial layers.

The application of the pharmaceutical formulation of the invention and the subsequent application of a layer of thermal mud on the skin regions where the formulation had been previously applied determine a faster trans-dermal passage of the pharmaceutical exalting the ability of the thermal mud because of its intrinsic quality and especially for biological effect of the bio-reactor defined in the application area.

In particular, Abano Montegrotto thermal mud is prepared by collecting clay from the bottom of two thermal lakes and putting it in vessels for the maturation period, developing in two months in presence of a continuous flux of thermal water at a temperature of 85°-87° C. During this maturation process, muds are colonized by cyanobacteria and microseaweeds that impart specific chemical-physical features. The features of this thermal mud are known thanks to a plurality of scientific publication in particular by University of Padova, Faculty of Medicine and collected by the Centro Studi Termali "Pietro D'Abano".

Clay changes into mature muds thus increasing its lipid and water content, increasing thermoinsulation, with the appearance of diatomeae and cyanoficeae, seaweeds present in Abano-Montegrotto thermal ecosystem and especially a bacterial colonization of micro-organisms, in particular cyanobacteria including Phormidium.

In particular this cyanobacterium is able to produce glycolipid substances that perform a fundamental role in the therapeutic action of the thermal mud. Features of the mature thermal mud are evaluated taking into consideration the visco-elastic and structural features constituting the theological properties of the muds (RTM index, for the definition of which Italian patents N. IT1268654 and IT1282836, herein incorporated by reference, can be seen). Bioadhesivity of the muds to the skin and the tensiometric features of the thermal mud for the skin (TVS, for the definition of which Bettero A., of Benedetto M., Marcazzan M., Zancato M. and Semenzato A. (1998), An innovative technical form for bioadhesive topical application of active substances, Proc. XXth IFSCC, Cannes; Bettero A., Marcazzan M., Gregorio M. and Semenzato A. (1999), Nuove forme tecniche per l'applicazione topica bioadesiva e metodo per valutare in vivo and in vitro l'effetto bioadesivo indotto (Bioadhesivity test TVS), Atti Cony. Argille curative, Salke Terme/PV, October 26-28, pp. 145) and is measured by evaluating the superficial free energy and polar component of the muds.

The application of hot mature muds on the skin, at a temperature of 38-39° C., determines: an increase of the skin temperature of about 2-5° C., an increase of the temperature of the subskin and of the dermis of about 1-3° C., an increase of the muscular sinew temperature and in particular of about 1-2° C. From all of these a vasodilatation of the zones affected by the increase in temperature, with better vascularization and an increase in cell metabolic exchanges.

It is determined an increase of ionic exchanges through the skin in both isotrophic and ectotrophic directions, is a mechanism that is very important for the aims of the present invention.

At a systemic level, a slight increase of the cardiac frequency, increase of the body temperature, skin vasodilatation, decreased concentration of oxyhemoglobin in the venous blood, enzymatic activation, a decrease in the level of creatinine, trglycerides, cortisol, and alkaline phosphatase. Renal functionality improves and with sudoration the quality of circulating liquid decreases, with a better redistribution of the intra and extracellular liquids.

The effect of the mud therapy causes a neuro-immuno endocrine response manifested by an important increase in the blood of ACTH and beta endorphin.

This chain of physical and biochemical and biohormonal events is nothing but the effect of the natural bioreactor happening in the thermal site.

EXAMPLE 3

Preparation of a First Formulation According to the Invention

An amount of 100 g of a creamy formulation according to the present invention was prepared by mixing together at ambient temperature 10 g of alfalfa herb in form of dry extract and derivatives thereof, in particular pyroGU-TYR-PRPO amide tripeptide (5 µg), and an amount of 10 mg of melatonin, together with water and other excipients and other natural substances, in particular chosen amongst ginkgo bilobate, avocado, blueberry, centella, fucus, glycerine, caffeine, extract of Centella asiatica, escine, tocopherol, dextrin, lecithin, tocopherol acetate, phospholipids, cyclodextrins, oils and natural active principles. Components were mixed until a homogeneous creamy compound was obtained.

EXAMPLE 4

Preparation of a Second Formulation According to the Invention

An amount of 100 g of a creamy formulation according to the present invention was prepared mixing together at ambient temperature 20 g of alfalfa herb in form of dry extract and derivatives thereof, in particular pyroGlu-Tyr-Proamide tripeptide (10 µg), and an amount of 10 mg of melatonin, together with water and other excipients and other natural substances, in particular chosen amongst ginkgo bilobate, avocado, blueberry, centella, fucus, glycerine, caffeine, extract of Centella asiatica, escine, tocopherol, dextrin, lecithin, tocopherol acetate, phospholipids, cyclodextrins, oils and natural active principles. Components were mixed until a homogeneous creamy compound was obtained.

EXAMPLE 5

Application of the Formulation According to the Invention

The formulation (cream) based on alfalfa herb and melatonin according to the invention is applied on the skin, in a zone affected by cellulite and/or localized adiposity, according to an amount depending on the width of the zone itself and the capacity of absorption of the skin. The affected body zone must be massaged in order to allow for a better and more homogeneous distribution of the product on the surface of the skin, the massage allowing for absorption and transdermic passage of some components of the used product, and at the same time the massage having the effect of stimulating the vascularization of the subcutaneous tissue with manual mechanical compressions to assist the circulation to the tissues and the draining of lymphatic fluid. This aspect is fundamental for the efficacy of the product In a second step, according to a preferred embodiment of the present invention, on the zones of skin previously treated was applied an homogeneous layer having a thickness of some millimeters of Abano Montegrotto thermal mud or of other vegetal or mineral muds enriched with the same active principles (melatonin (0.005% by weight) and alfalfa herb (5-10% by weight) present in the cream, and optionally further comprising excipients chosen between zinc oxide, glycerine, caffeine, tocopherol, lecithin, waterpuncite, silica aluminate, sepiolite, essences and natural active principles, seaweeds, active thermal water.

The thermal mud provides an action on the skin that can be compared to the bioreactor so as to allow for a faster passage of the substance in to layers deeper than the subcutaneous layer, in particular to the adipose cells.

Actually the adipose cell is a metabolically active cell playing a central role in controlling the energetic balance of the organism. In its membrane the receptors are present to which different hormones having lipogenic (insulin, estrogens) or lipolytic (thyroidal, surrenalic, androgen hormones) can bind.

Triterpenic saponins and in particular pyroGLU-TYR-PRO amide tripeptide, appears to be very similar to human TRH, being different only because of the substitution of tyrosine with histadine in position 2. This tripeptide is contained in the alfalfa herb and it has a strong lipolytic function.

Melatonin has a synergistic action with alfalfa herb that in turn stimulates the functions of the pineal gland producing endogenous melatonin and is responsible of the neuro-immuno-endocrine maintenance of the biological clock in man.

Melatonin for topical use has an important antioxidant effect on the skin and is useful in the treatment of skin aging.

If muds are not obtained from the thermal site, with the described effects of the natural bio-reactor, it is possible as an alternative to use inert natural muds with the addition of alfalfa herb and melatonin at the same concentration as that of the cream.

The anti-cellulite effect is manifested by the lipolytic action developed at a regional level by the substances applied on the skin with removal of fats by digestion or by the kidneys.

EXAMPLE 6

Protocol of Application of the Formulation According to the Invention and Results Some volunteers with an age comprised between 20 and 70 years were recruited. The patients were subjected to the following screening before and after the treatment:

Creatinine; glucose; cholesterol; HDL; LDL; triglycerides; amylase; lipase; transaminase; $Ft_3$; $Ft_4$; TSH; electrolytes (Ca, Na, K, Fe,); Plicometric exam; Measurement of the circumferences; Impedenzometric exam; DEXA; Ecography; and Photographic exam.

The formulation, in form of a cream, was applied on the affected skin zone and massaged for at least 20 minutes, so to allow a complete absorption. Thereafter, on the same zone muds were applied, keeping it the zone covered with a suitable plastic sheath for at least 20-30 minutes.

Thereafter, the patient was allowed to have a shower. The treatment was performed 2/3 times a week until 15 applications were made.

During the treatment, the patients were required to maintain the same eating habits and lifestyle.

Clinical trials were performed in two centres, applying the same criteria of selection and evaluation of the patients.

A first group of patients was treated in the private medical ambulatory clinic of Prof. Giulio Bellipanni, in collaboration with the University of Roma—Tor Vergata, Policlinico Universitario.

A second group of patients was treated in the private Clinic of the Marc Messegue Health Center of Melezzole (TR), with daily treatments for 7/10 days.

The first group of patients, composed of 14 people 21 to 65 years of age (average age 39 years), was subjected to a study in order to evaluate the possible variation of the weight of fat mass, of lean mass and of the percentage of body fat after topical application of the formulation according to the present invention.

The formulation, in form of a cream, was applied twice every week for an average time of 45 days.

All the recruited patients were subjected to a preliminary medical visit and clinical and instrumental controls. In particular, in collaboration with the endocrinology out patient department of the University of Tor Vergata, DEXA exam was performed before and after the treatments to evaluate their efficacy.

DEXA exam is based on the principle of differential attenuation of a beam of X-rays at two energetic levels, when passing through the tissues. This attenuation was registered and correlated to the body composition of the subject. DEXA exam allows to evaluate, in a very reliable way and is only slightly influenced by differences due to the operator, the weight and percentage of fat mass and lean mass in different body zones.

The analysis of the data collected by DEXA exam showed a decrease of the weight of fat mass in 7 patients, corresponding to 50% of the sample, an increase of lean mass in 6 patients, corresponding to 43% of the sample, and a decrease of the percentage of fat in 7 patients, corresponding to 50% of the sample treated.

As a whole, it was measured a loss of weight of fat mass of 8.806.2 grams, corresponding to 7.4% of the average weight of the fat mass at first control. On the contrary lean mass increased as a whole of 7.688.9 grams, corresponding to 3.6% of the weight of lean mass at first control.

In 50% of the patients treated a decrease of the weight and of the fat mass was detected as an average of 7.4%, and a decrease of the percentage of fat of 50%.

The second group of patients, treated at Marc Messegue Health Center and composed of 10 patients between 23 and 69 years of age (average age 41 years), was studied in order to evaluate possible variations of the weight of fat mass, of lean mass and of the percentage of body fat after topical application of the formulation in cream according to the invention for 7/10 days.

All the recruited patients were subjected to a preliminary medical visit and clinical and instrumental controls.

The analysis of the data collected by means of impedenziometric exam, before and after the cycle of applications, showed a decrease of the weight of fat mass in 8 patients, corresponding to 89% of the sample, an increase of lean mass in 6 patients, corresponding to 67% of the sample, and a decrease of the percentage of fat in 7 patients, corresponding to 78% of the sample treated.

As a whole, the loss of fat mass was 9.900 grams, corresponding to 5.4% of the average weight of the fat mass at first control, while lean mass increased as a whole of 10.000 grams, corresponding to 5.8% of the weight of lean mass at first control.

Abdominal circumference detected at the level of the navel showed an average decrease of 3 cm on 80% of the sample. Only in two occasions it was not shown a decrease of the circumference.

Also a plicometric exam showed an average decrease of 3.5% on 80% of the sample.

The present invention was described for illustrative, non-limitative purposes, according to its preferred embodiments, but it is to be understood that any variation and/or modification can be made by the skilled in the art without for this reason escaping the relative scope of protection, as defined by the enclosed claims.

The invention claimed is:

1. A creamy topical formulation for the treatment of cellulite where said formulation consists of water, alfalfa herb and melatonin, wherein said alfalfa herb is in the form of a dry extract, in an amount between 5 and 40% by weight of the total weight of the formulation and melatonin in an amount between 0.01 and 0.1% by weight of the total weight of the formulation.

* * * * *